United States Patent
Bouvier et al.

(10) Patent No.: US 9,649,077 B2
(45) Date of Patent: May 16, 2017

(54) MEDICAL IMAGING SYSTEM WITH C-ARM AND PROTECTION COVER SUPPORTED BY TWO DIFFERENT VEHICLES

(75) Inventors: Bernard Bouvier, Buc (FR); Romain Moulin, Buc (FR); Jean-Michel Marteau, Buc (FR); Vincent Croulard, Buc (FR); Omar Al Assad, Buc (FR); Bruno Galloni, Buc (FR); Stephane Graziani, Buc (FR); Gilles Robin, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 193 days.

(21) Appl. No.: 14/410,935

(22) PCT Filed: Jun. 29, 2012

(86) PCT No.: PCT/IB2012/001338
§ 371 (c)(1),
(2), (4) Date: Dec. 23, 2014

(87) PCT Pub. No.: WO2014/001834
PCT Pub. Date: Jan. 3, 2014

(65) Prior Publication Data
US 2015/0201893 A1 Jul. 23, 2015

(51) Int. Cl.
*H05G 1/02* (2006.01)
*A61B 6/00* (2006.01)
*A61B 6/10* (2006.01)

(52) U.S. Cl.
CPC ............ *A61B 6/4405* (2013.01); *A61B 6/102* (2013.01); *A61B 6/4441* (2013.01); *A61B 6/4411* (2013.01); *A61B 6/4447* (2013.01)

(58) Field of Classification Search
CPC ....... A61B 6/4441; A61B 34/20; A61B 6/032; A61B 6/12; A61B 6/504; A61B 46/10;
(Continued)

(56) References Cited

U.S. PATENT DOCUMENTS 6,113,264 A   9/2000  Watanabe
6,203,196 B1*  3/2001  Meyer .................. A61B 6/4464
                                              378/197

(Continued)

FOREIGN PATENT DOCUMENTS

CN       1571648 A    1/2005
JP       02228946 A   9/1990
(Continued)

OTHER PUBLICATIONS

Unofficial English Translation of Chinese Office Action issued in connection with corresponding CN Application No. 201280074392.5 on May 5, 2016.
(Continued)

*Primary Examiner* — Irakli Kiknadze
(74) *Attorney, Agent, or Firm* — GE Global Patent Operation; Marc A. Vivenzio

(57) ABSTRACT

A medical imaging system comprising a C-arm supporting a radiation source and a radiation detector, an external protection cover of said C-arm, wherein said C-arm and said cover are separable from each other and are respectively supported by two different vehicles when separated from each other.

20 Claims, 10 Drawing Sheets

(58) Field of Classification Search
CPC ... A61B 90/36; A61B 2090/376; A61B 6/481; A61B 2034/2055; A61B 6/4423; A61B 6/503; A61B 6/547; A61B 5/055; A61B 6/4233; A61B 6/4452; A61B 6/102; A61B 6/4405; A61B 6/4411; A61B 6/4447; A61B 6/035; A61B 6/4021; A61B 6/4429; A61B 6/4464; A61B 6/588; A61B 6/02; A61B 6/037; A61B 6/04; A61B 6/4014; A61B 6/4258; A61B 6/487; A61B 6/461; A61B 6/5205; A61B 6/54; A61B 6/0407; A61B 6/463; A61B 6/542; A61B 6/06; A61B 6/107; A61B 6/0457
USPC .................. 378/4, 15, 20, 62, 208, 196–198
See application file for complete search history.

(56) References Cited

U.S. PATENT DOCUMENTS

| | | | | |
|---|---|---|---|---|
| 6,619,840 | B2* | 9/2003 | Rasche | ............... A61B 6/032 378/196 |
| 6,940,941 | B2* | 9/2005 | Gregerson | ............ A61B 6/032 250/363.05 |
| 7,748,900 | B2 | 7/2010 | Maschke | |
| 2003/0072416 | A1 | 4/2003 | Rasche et al. | |
| 2004/0022350 | A1 | 2/2004 | Gregerson et al. | |
| 2005/0054915 | A1* | 3/2005 | Sukovic | ............... A61B 6/032 600/424 |
| 2008/0192885 | A1* | 8/2008 | Teofilovic | ............. A61B 6/035 378/4 |
| 2013/0240402 | A1* | 9/2013 | Campista | ................ B32B 7/12 206/525 |

FOREIGN PATENT DOCUMENTS

| | | |
|---|---|---|
| JP | 04131213 U | 12/1992 |
| JP | 10216118 A | 8/1998 |
| JP | 10328173 A | 12/1998 |
| JP | 2005177047 A | 7/2005 |
| JP | 2008018240 A | 1/2008 |

OTHER PUBLICATIONS

Unofficial English Translation of Japanese Office Action issued in connection with corresponding JP Application No. 2015-519363 on May 10, 2016.
A PCT Search Report and Written Opinion issued in connection with corresponding Application No. PCT/IB2012/001338 on May 6, 2013.

* cited by examiner

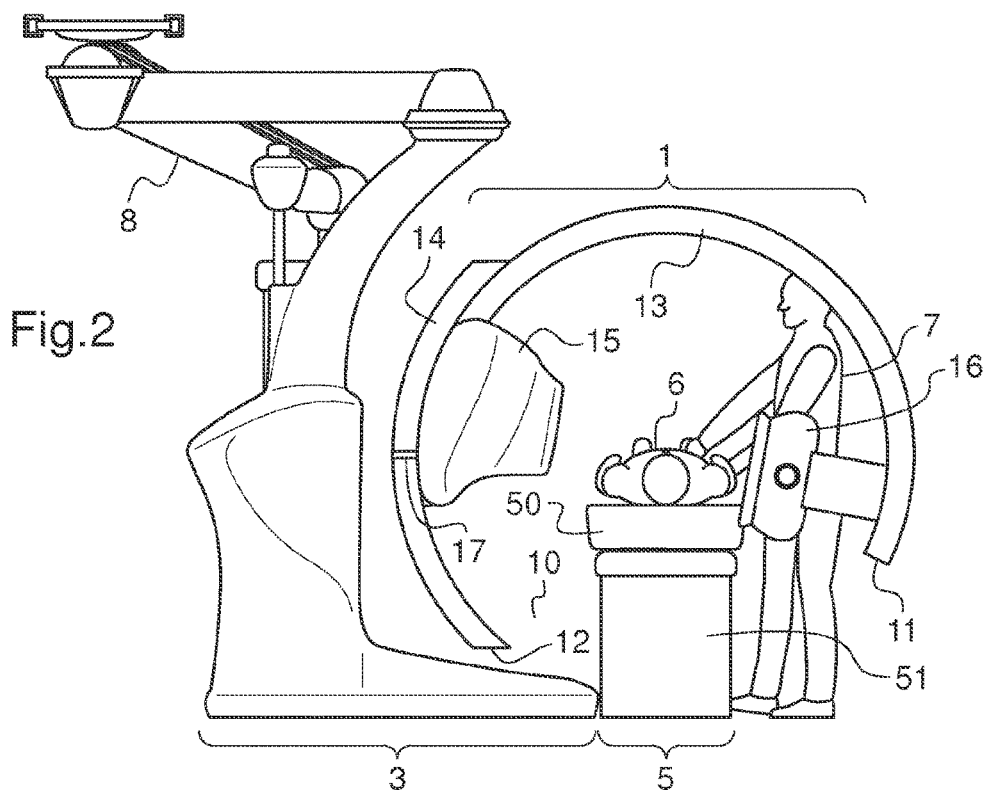
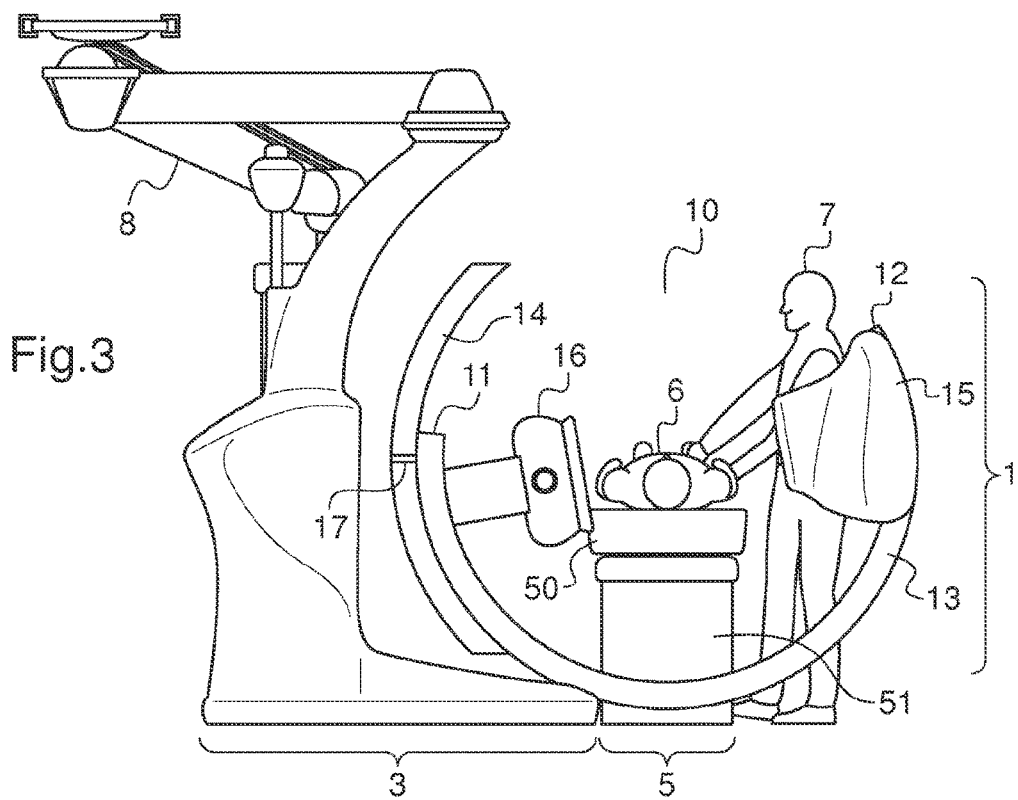

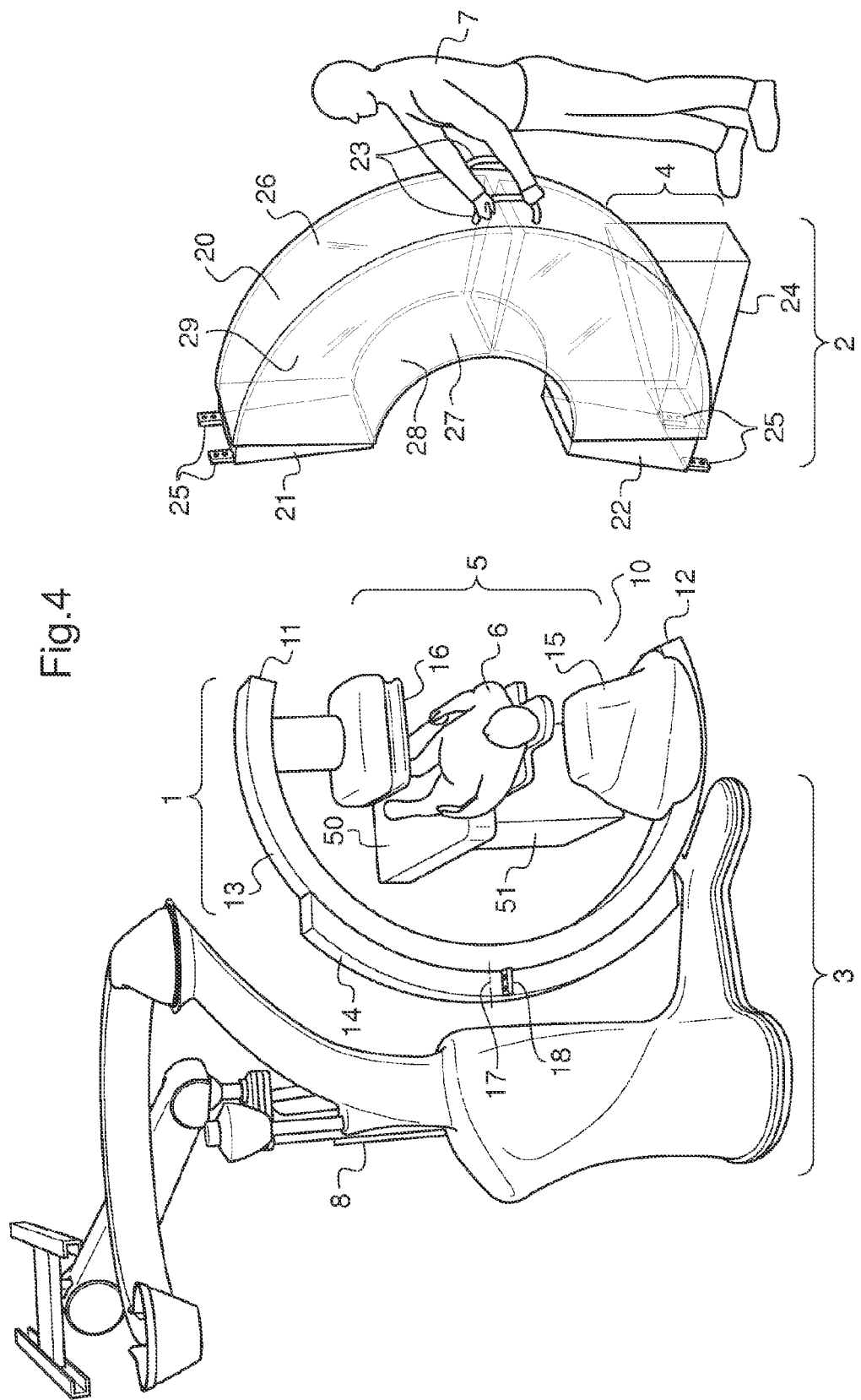

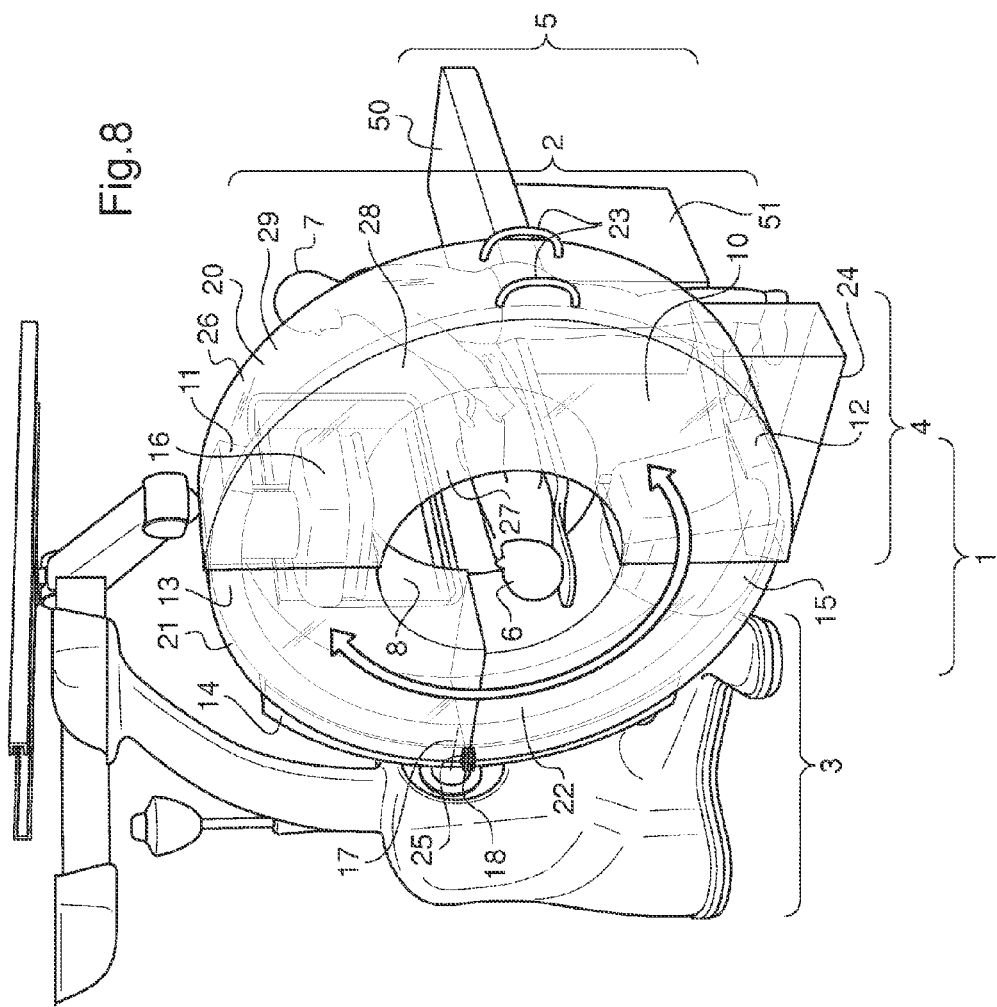

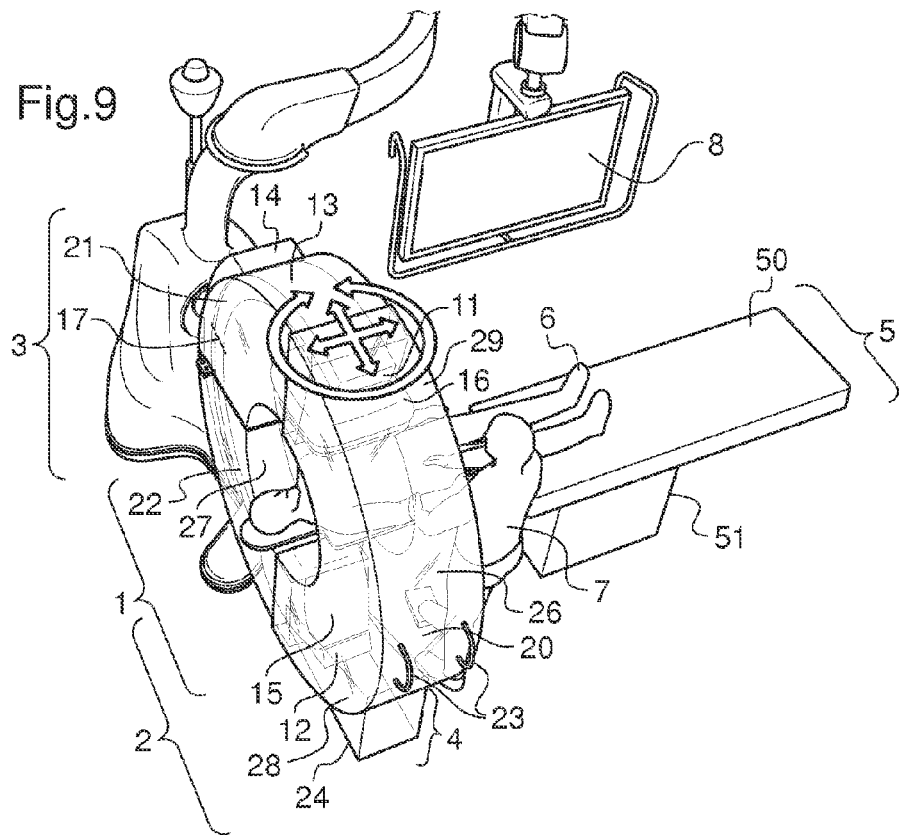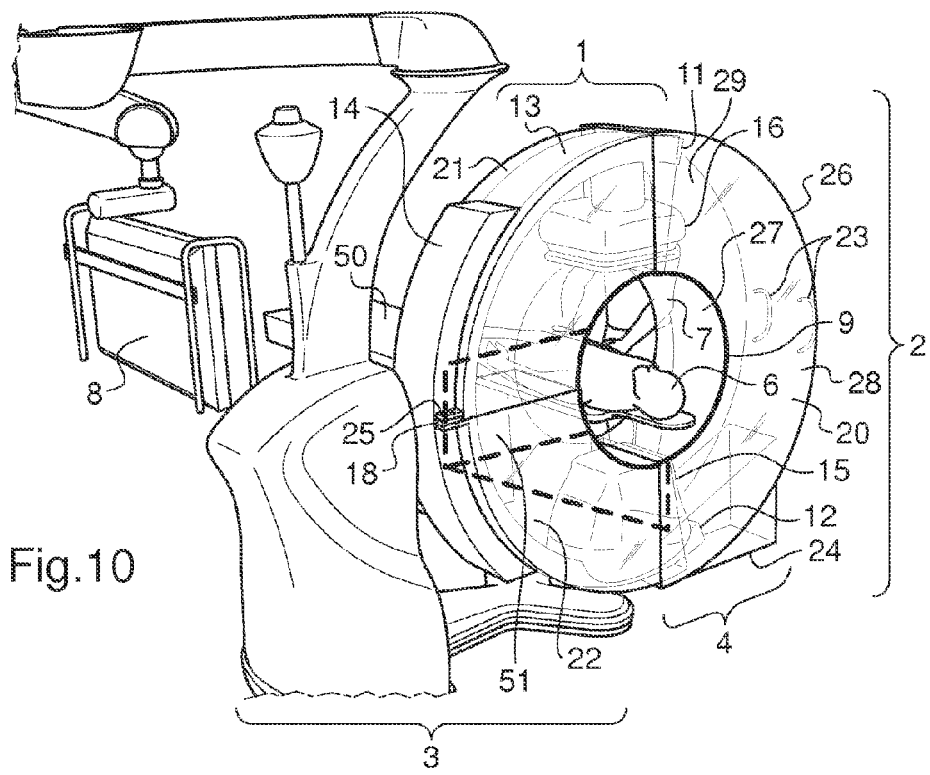

MEDICAL IMAGING SYSTEM WITH C-ARM AND PROTECTION COVER SUPPORTED BY TWO DIFFERENT VEHICLES

FIELD OF THE INVENTION

The invention relates to medical imaging systems comprising a C-arm and a protection cover of this C-arm. This protection cover encompasses part of this C-arm and allows for protection against collisions coming from certain directions.

BACKGROUND OF THE INVENTION

In a medical imaging system, the C-arm is a mobile arch which supports both the radiation source and the radiation detector. Radiation is usually X-ray. To provide images which can be simple photos, films, axial or lateral three dimensional, or four dimensional, or long three dimensional volumes thanks to helical acquisition, this C-arm can be moved and rotated along more or less complicated paths.

Medical imaging systems can be of different types. A Computed Tomography apparatus will capture one or several thin sections of a part of a human body and will provide a three dimensional image. An Interventional system will either provide a three dimensional image of a volume of a part of a human body or a film in a fluoroscopy mode. It can also provide a simple photo, which means a single shot. A Radiological system will provide a simple photo a part of a human body.

To check that no collision can occur with any object that would be on the trajectory of any part of the C-arm, most often in the prior art, a first move or rotation of the C-arm along the projected trajectory is performed at quite a slow speed, before performing it at high speed required to capture the needed images. This preliminary checking operation is laborious, all the more that it has to be performed often; indeed, and it has to be performed at least each time a new trajectory of the C-arm move is projected.

The main move of the C-arm will be a rotation around a virtual axis which roughly corresponds to the center of the C form of the C-arm. Since the C-arm is no full circle but only a part circle, when it rotates, and especially when it rotates at high speed, it means that any object crossing the trajectory of the rotation in the circular gap between the two ends of the C-arm will lead to a severe collision which should be avoided. Several prior art pieces have tried and tackled this collision avoidance in the gap of the C-arm during C-arm rotation, but none appears to be fully satisfactory.

According to a first prior art, for example described in U.S. Pat. No. 6,203,196, it is known a modular medical imaging system in which a full inner C of C-arm can be set up. Therefore, collision risk of an object coming in the gap of a partial inner C of the C-arm is successfully avoided. However, there is no efficient protection against other potential collisions, whatever the direction they are coming from. In some embodiments, the complementary part of the C-arm inner C is integral with the C-arm inner C, what makes the global system too cumbersome when the full inner C is not needed. Moreover, this integral structure with relatively mobile parts does not help with respect to vibration aspect.

According to a second prior art, for example described in patent application US 2003/0072416, it is known a modular medical imaging system in which a full protection outer C of C-arm can be set up. Therefore, collision risk of an object coming in the gap of a partial inner C of the C-arm is successfully avoided. Therefore, collision risk of an object coming from outward the C-arm is successfully avoided too. However, there is no efficient protection against some other potential collisions, especially when coming from inwards the C-arm inner C, what notably corresponds to the situation of body fluids, like for example urine or blood, projection from patient or from a moving part of a patient body, like chest or arm. In all embodiments, the outer protection cover of the C-arm inner C is integral with the C-arm inner C, what makes the global system too cumbersome when the full outer protection ring is not needed. Moreover, this integral structure with relatively mobile parts does not help with respect to vibration aspect.

According to a third prior art, for example a complete Computed Tomography apparatus, it is known a one piece medical imaging system in which a full protection inner and outer C of C-arm can be set up. Therefore, the collision risk is correctly tackled. But in many use configurations, the added complexity is much higher to the needed security requirements, what 10 practically makes this apparatus not usable or hardly usable for those use configurations. This apparatus is no multi-use apparatus but an apparatus dedicated to one type of image capturing mode.

SUMMARY OF THE INVENTION

The object of the present invention is to alleviate at least partly the above mentioned drawbacks. More particularly, the invention aims to tackle successfully this collision avoidance in the C-arm gap when rotating. The invention also aims at tackling one or more other collision avoidance problems at the same time. While tackling this security problem with high security requirements, the invention still aims at providing a not too bulky, not too cumbersome and or not too unpractical global medical imaging system. In particular, the test phase rotating the C-arm first at low speed to check the collision risk will become practically useless and can be skipped.

The invention globally can be seen as aiming at solving a delicate compromise for this medical imaging system, which is meeting high security requirements with respect to collision avoidance, while still providing an apparatus rather practical and light to use, all the more that the invention aims at solving this delicate compromise not only in one use configuration, but in several use configurations. Different use configurations correspond notably to different types of captured images, like for example one shot simple photos, films, axial or lateral three dimensional, or four dimensional.

Previous attempts in discussed prior art either present some lacks with respect to collision avoidance security, or are rather bulky and or cumbersome and or unpractical, for at least one or more use configurations when capturing medical images. Even when providing a modular medical imaging system implementing a C-arm protection cover, previous attempts of prior art were unsuccessful or not successful enough.

According to the invention, it has been noticed that modifying the type of modularity in the medical imaging system and or modifying the structure and, in an embodiment, the form of the protection cover, would render such attempts more successful.

Embodiments of the invention will first modify the type of modularity in the medical imaging system, and then, in an embodiment, modify the structure and, in an embodiment, the form of the protection cover too.

When alleviating the bulky, cumbersome and or unpractical aspects of this medical imaging system, the invention takes into account the sterility aspect which means lowering the contamination risk of the medical imaging system by contamination agents, like dirt, urine or blood, mainly due to projections of the patient under examination. Lowering the contamination risk of the medical imaging system is done by lowering the exposure to contamination agents and by making easier the cleaning if exposed to such contamination agents. Therefore, the modified modularity in the medical imaging system helps lowering the exposure to contamination agents, since the protection cover, when not needed, is no more in the neighborhood of the patient. Therefore, in a similar way, the modified structure and or modified form of the protection cover in the medical imaging system helps making easier the cleaning of the protection cover and of the C-arm when they have been exposed to such contamination agents.

According to the invention again, it has been noticed that modifying the type of modularity in the medical imaging system and or modifying the structure and, in an embodiment, the form of the protection cover, would help improving sterility aspect. This is true, especially because, when open so when more exposed to be contaminated in a way harder to clean, the protection cover is, in an embodiment, more often removed far from patient neighborhood.

More specifically, embodiments of the invention, while solving the problem of collision of objects coming in the gap of the C-arm when rotating, aim at solving at the same time the problem of providing a rather light and rather practical modular apparatus which, for the highest possible number of use configurations, provides a satisfying or very satisfying level of collision avoidance to the expense of a low added complexity to the apparatus. To meet this objective, modularity of the medical imaging system has been successfully challenged in the sense that the added complexity remains in correspondence with the needed collision avoidance security level, and that for several, and, in an embodiment, for all, use configurations. Specific modularity helps adding, in an embodiment, no more or practically no more complexity than needed to reach a needed collision avoidance security level in a particular use configuration. The protection cover is not present in all use configurations.

Preferably even more specifically, embodiments of the invention, while solving the problem of collision of objects coming in the gap of the C-arm when rotating, also aim at solving at the same time the problem of lowering the risk of collision between a potentially outwards protruding part of the patient to be examined and lying on the table, like his or her arm for example, and a inwards protruding part of the C-arm, mainly either the radiation source or the radiation detector, for one or more use configurations and, in an embodiment, for the highest possible number of use configurations.

Embodiments of the invention provide a unique solution to a compromise hard to tackle. Then, indeed, more aspects of collision avoidance, and not only the C-arm inner gap aspect, are treated, while keeping a level of added complexity more adapted to each specific use configuration, while managing at the same time the sterility aspect not taken into account in prior art which needs specific additional complexity therefore, whereas in said embodiments of the invention, all these positive results are reached through type of modularity of medical imaging system combined with structure of protection cover.

The invention can also be seen as providing an intermediate apparatus situated somewhere between the classical Interventional gantry and the classical Computed Tomography gantry, as far as complexity is concerned. It provides many functions of both these classical apparatuses are provided, its structural protection and modularity features helping to adapt the complexity of the used part of the apparatus to the use configuration.

This object is achieved with a medical imaging system comprising a C-arm supporting a radiation source and a radiation detector, an external protection cover of said C-arm, wherein said C-arm and said cover are separable from each other and are respectively supported by two different vehicles when separated from each other.

In an embodiment, said C-arm includes a mobile inner C supporting said radiation source and said radiation detector, wherein said cover is removable from said C-arm, and wherein said cover is expandable into a tunnel encompassing the full rotation path of said inner C, of said radiation source and of said radiation detector, so as to protect said full rotation path both from inwards and from outwards of said inner C.

Preferred embodiments comprise one or more of the following features which can be used alone, part of them in combination or all of them in combination.

Both vehicles can be vehicles moving on the ground, for example with the help of wheels. Both vehicles can be vehicles moving close to the ceiling, for example with the help of rails fixed to the ceiling. One of the vehicles, either the vehicle supporting the C-arm or the vehicle supporting the protection cover, can be a vehicle moving on the ground, whereas the other vehicle, either the vehicle supporting the protection cover or the vehicle supporting the C-arm, can be a vehicle moving close to the ceiling.

In an embodiment, said vehicles are both vehicles moving on the ground, in an embodiment, with the help of wheels. Such vehicles are less bulky than vehicles moving close to the ceiling, for example on rails fixed to the ceiling, and can move more easily. Besides, such vehicles moving on the ground have less negative impacts on the sterile laminar flow around the patient than vehicles guided close to the ceiling from which dirt particles can more easily fall on the patient or in the neighborhood of the patient.

In an embodiment, said vehicle supporting said cover includes a C-arm rotation guiding system. This allows for increasing the rotation speed of the C-arm inner C.

In an embodiment, said vehicle supporting said C-arm is an automated guided vehicle. In an embodiment, said vehicle supporting said C-arm includes the full image chain from said radiation source to said radiation detector.

In an embodiment, in a first family of embodiments in which the structural simplicity and the bulkiness of the protection cover are optimized, said vehicle supporting said cover is a manually guided vehicle. In an embodiment, said vehicle supporting said cover is a manually moveable vehicle. In an embodiment, said vehicle supporting said cover is a powerless vehicle. In an embodiment, said cover includes one or more free wheels. In an embodiment, said cover includes one or more handles.

In an embodiment, in a second family of embodiments in which the ease of uses for medical staff is optimized, said vehicle supporting said cover is an automated guided vehicle. This allows for a very ergonomic and flexible way of removing the protection cover from the C-arm neighborhood to store it elsewhere and of installing it by locking it to the C-arm starting from a parking place which can be not in the immediate neighborhood of the C-arm. The possibility to locate the parking place of the vehicle supporting the protection cover not in the immediate neighborhood of the C-arm helps avoiding contamination agents coming from patient to contaminate this protection cover which, in turn, could more easily contaminate next patient. In an embodiment, said vehicle supporting said cover can be automatically guided toward said vehicle supporting said C-arm.

In an embodiment, said vehicle supporting said cover can be automatically guided toward said vehicle supporting said C-arm via a pre-calculated path which is automatically calculated from parking positions of both said vehicles. This makes more flexible and practical the process to remove protection cover from C-arm or to install protection cover around C-arm.

In another embodiment, said vehicle supporting said cover can be automatically guided toward said vehicle supporting said C-arm via a predetermined path. This makes even more flexible and practical the process to remove protection cover from C-arm or to install protection cover around C-arm.

In an embodiment, said vehicles can be connected together so that an outer C of said C-arm and said cover can come to a rest relatively to each other. In an embodiment, one of said vehicles can be locked on the other of said vehicles via a locking system which locks one or more mobile parts of said cover on an outer C of said C-arm. This allows for an increased rigidity better to lower vibrations, especially at high rotation speed.

In an embodiment, said vehicles can be connected together so as to be able to move as one single vehicle. While having the flexibility of a completely removable protection cover when not needed, this allows at the same time also for flexibility of use when needed.

Some embodiments comprise one or more of the following features which can be used alone, part of them in combination or all of them in combination. These features can be combined in all or in part to some or all of the features previously described.

In an embodiment, said cover is expandable into a tunnel completely encompassing the full rotation path of said inner C, of said radiation source and of said radiation detector, so as to protect said full rotation path from all directions. That way, the effective protection of C-arm against contamination agents is increased.

The presence of a protection cover encompassing the rotation path, 5 and especially protecting the rotation path from inwards, that is to say from inner the partial circle constituted by the C-arm, allows for reducing the free space between patient and between C-arm, especially between patient on the one side and source and detector on the other side. Thanks to the protection cover, this reduction of free space can be done safely.

The presence of a protection cover presents the advantage of allowing quick switch from an image to another image. For example, during insertion of a needle, it is interesting to be able to switch from an image showing the insertion direction of the needle along the needle, to an image showing the progression of the needle perpendicularly to the needle. Of course, to be able to switch easily from one of these images to the other of the images, both those directions along and perpendicular to the needle should be in the plan of the protection cover which is, in an embodiment, roughly circular to protect the C-arm.

In an embodiment, said rotation path of said inner C allows for lateral three dimensional imaging. That way, access for tubing the patient is made easier.

In an embodiment, said cover includes one or more free wheels. In an embodiment, said cover includes one or more handles. This allows for a manually guided cover which can simply and easily be removed or implemented.

In an embodiment, said mobile inner C is rotary mobile so as to rotate alternatively clockwise and counterclockwise. This alternate rotation could be performed continuously without any pause or stop between each period. The rotation speed of the C-arm inner C can be increased thanks to the efficient protection cover.

In another embodiment, said mobile inner C is rotary mobile so as to rotate continuously clockwise or to rotate continuously counter-clockwise. The rotation speed of the C-arm inner C can be increased even more that way thanks to the efficient protection cover. The presence of a protection cover allows for performing more safely quick alternate rotation or quick continuous rotation, because of the collision risk being notably reduced if not practically cancelled.

In an embodiment, it includes a locking system which locks one or more mobile parts of said cover on an outer C of said C-arm. This helps making the global medical imaging system more rigid, what will be all the more useful to lower vibrations that the rotation speed of the C-arm inner C is high.

In an embodiment, said C-arm comprises a collision detecting system which is disconnected when said locking system is locked and or said C-arm rotation speed is increased when said locking system is locked. Once the protection cover is implemented, rotation speed can be increased safely, and the collision system of the C-arm itself becomes useless or at least of little use.

In an embodiment, said expandable cover is telescopic. In an embodiment, said expandable cover presents a half ring form which can be expanded into a full ring form. In an embodiment, said one or more mobile parts include two quarters of ring which can respectively spread from both ends of said half ring. This is a simple and efficient expandable structure for the protection cover.

In one embodiment, said cover includes one or more mobile parts which can be stored inside said half ring and which can be spread outside said half ring. In this embodiment, the expansion mechanism is very simple.

In one embodiment, said cover includes one or more mobile parts which can be stored outside said half ring and which can be retracted when spread outside said half ring so as to present the same section as said half ring, in a way similar to a sliding door of a vehicle. In this embodiment, the overall dimensions of the protection cover can be reduced.

In an embodiment, said cover is in material which is transparent when said C-arm is immobile and which is opaque at least when said C-arm is rotating above a speed threshold, and which is, in an embodiment, opaque when C-arm is rotating. This transparency feature, when the C-arm is immobile, helps for medical staff to install the patient on his or her table, around the whole medical imaging system with its accessories. The protection cover is no visual hindrance during installation phase. This opacity feature when the C-arm is rotating or at least rotating fast, avoids the patient being disturbed by the quick rotation of the C-arm inner C and especially by the quick rotation 10 of both the radiation source and the radiation detector, during imaging phase. Notably this advantageous feature of switching between transparency and opacity for the C-arm protection cover can also be used in any C-arm protection cover independently from all the rest of the invention.

In an embodiment, the protection cover includes its own collision detecting system. In an embodiment, this collision detecting system is made active only when the protection cover is locked on the C-arm. Preferably this collision detecting system is a collision detecting system located on an inner C of the protection cover in order to avoid collision of the patient or of the table with the interior of the protection cover when the group comprising the C-arm and the protection cover locked on the C-arm rotate in lateral three dimensional imaging.

In an embodiment, the distance between the external surface of the C-arm and the internal surface of the protection cover ranges from 5 mm to 20 mm, and is advantageously about 10 mm.

Further features and advantages of the invention will appear from the following description of embodiments of the invention, given as nonlimiting examples, with reference to the accompanying drawings listed hereunder.

BRIEF DESCRIPTION OF THE DRAWINGS

FIG. 2 shows a face view of an example of an automated guided vehicle supporting a C-arm in a medical system according to an embodiment of the invention, the C-arm being in clockwise extreme position of its alternate rotation.

FIG. 3 shows a face view of an example of an automated guided vehicle supporting a C-arm in a medical system according to an embodiment of the invention, the C-arm being in counter-clockwise extreme position of its alternate rotation.

FIG. 4 shows a view in perspective of an example of an imaging system according to an embodiment of the invention including an automated guided vehicle supporting a C-arm and a manually guided vehicle supporting a protection cover, both vehicles being separated from each other.

FIG. 8 shows a view in perspective of an example of an imaging system according to an embodiment of the invention including an automated guided vehicle supporting a C-arm and a manually guided vehicle supporting a protection cover, during rotation of the C-arm covered by its protection cover.

FIG. 9 shows a view in perspective of an example of an imaging system according to an embodiment of the invention including an automated guided vehicle supporting a C-arm and a manually guided vehicle supporting a protection cover, showing the possible moves of both vehicles connected together so as to be able to move as one single vehicle.

FIG. 10 shows a view in perspective of an example of an imaging system according to an embodiment of the invention including an automated guided vehicle supporting a C-arm and a manually guided vehicle supporting a protection cover, showing the collision detection system of the protection cover.

DETAILED DESCRIPTION OF THE INVENTION

Figure 1:
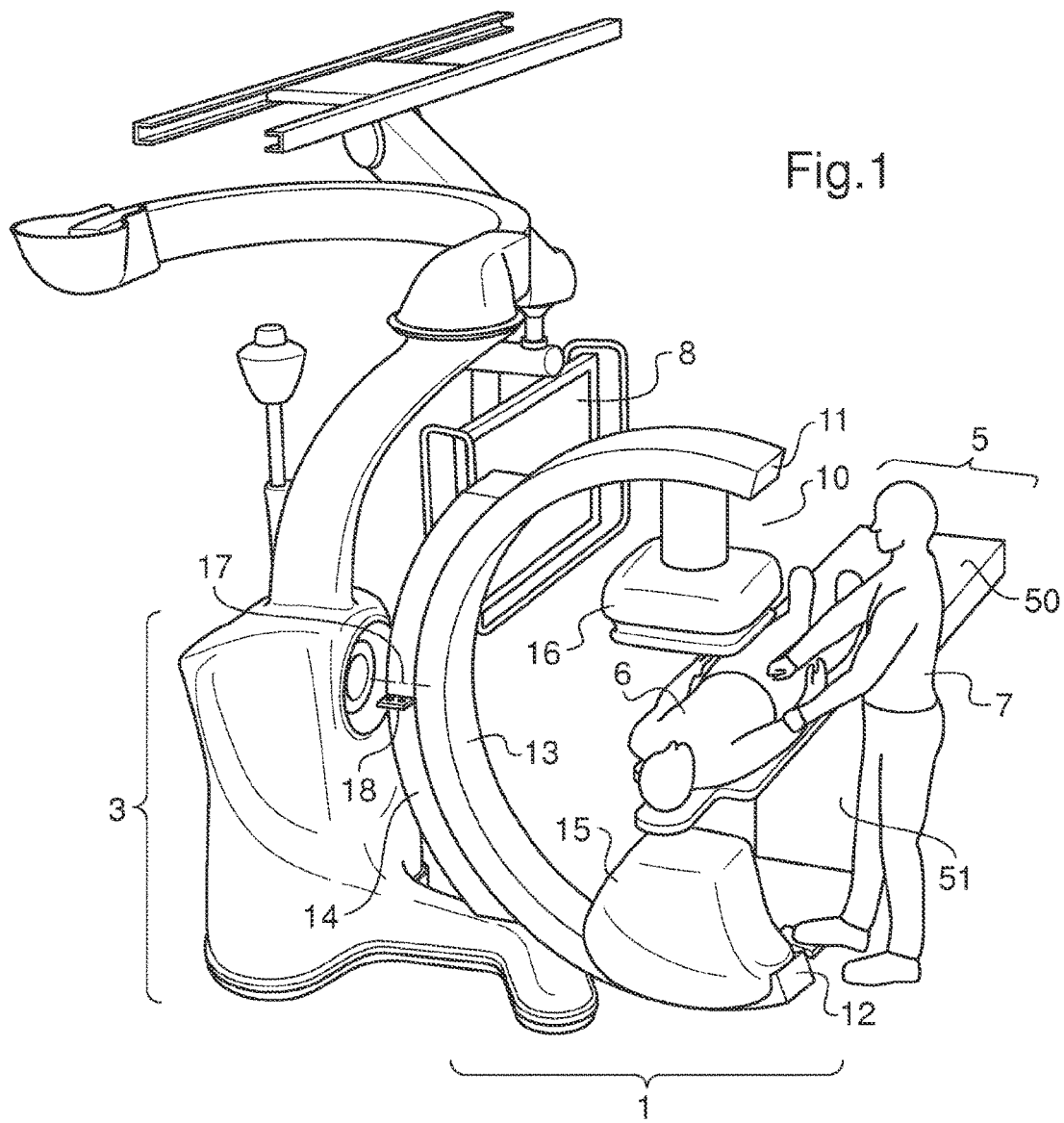
FIG. 1 shows a view in perspective of an example of an automated guided vehicle supporting a C-arm in a medical system according to an embodiment of the invention.

FIG. 1 shows a view in perspective of an example of an automated guided vehicle supporting a C-arm in a medical system according to an embodiment of the invention. The C-arm is oriented for lateral three dimensional imaging. An examination table 5 comprises a top 50 on which a patient 6 is lying. The top 50 is supported by a base 51. A medical operator 7 is managing the medical imaging system which he can command notably via a pedal. The part of the body of the patient to be examined is situated in the central region of the C-arm, more precisely in the central region of the gantry 1. The gantry 1 comprises an outer C 14 of the C-arm supporting a mobile inner C 13 of the C-arm, the mobile inner C 13 supporting in turn a radiation source 15 and a radiation detector 16. Outer C 14, inner C 13, radiation source 15 and radiation detector 16, belong to the gantry 1.

Radiation source 15 is fixed to lower end 12 of C-arm. Radiation detector 16 is fixed to upper end 11 of C-arm. Between both ends of C-arm, there is gap 10 especially critical with respect to collision risk as explained before. The C-arm comprises both outer C 14 and mobile inner C 13. The inner C 13 of the C-arm can slide along the outer C 14 of the C-arm. The inner C 13 of the C-arm has a circular rotation relative move with respect to the outer C 14 of the C-arm. The outer C 14 of the C-arm can rotate around an axis 17 supported by the vehicle 3. The outer C 14 of the C-arm also comprises a locking system 18 in its central region. A deported screen 8 and is supported by the ceiling via its articulation.

On FIG. 1, is represented a vascular type of X-ray apparatus. This apparatus comprises for example an X-ray tube 15 as well as an X-ray detector 16. This tube 15 emits an X-ray beam along a direction of emission, here vertical on the FIG. 1, bottom up. The tube 15 and the detector 16 are both hooked to the ends, on either side, of a C-arm. This C-arm, in the example of FIG. 1, is shaped like a hoop. The detector 16 is hooked to the C-arm opposite the tube 15 and in the direction of emission so as to receive the X-ray beam. The C-arm is connected to an L-shaped post 3 by means of a rotating axis 17. A collimator, situated at the end of tube 15 can be used to convey a shape to the X-ray beam emitted by the tube 15. Thus, the collimator could in particular modify the width of the beam.

FIG. 2 shows a face view of an example of an automated guided vehicle supporting a C-arm in a medical system according to an embodiment of the invention, the C-arm being in clockwise extreme position of its alternate rotation. It can be seen that the gap 10 position is changing during rotation of the C-arm, and that any object coming at any moment in this gap 10 will run a high risk of provoking a collision especially either with upper end 11 of C-arm or with radiation detector 16 during clockwise rotation of C-arm. The outer C 14 of the C-arm can rotate around an axis 17 supported by the vehicle 3, which axis 17 is horizontal in the plan of FIG. 2.

FIG. 3 shows a face view of an example of an automated guided vehicle supporting a C-arm in a medical system according to an embodiment of the invention, the C-arm being in counter-clockwise extreme position of its alternate rotation. It can be seen that the gap 10 position is changing during rotation of the C-arm, and that any object coming at any moment in this gap 10 will run a high risk of provoking a collision especially either with lower end 12 of C-arm or with radiation source 15 during counter-clockwise rotation of C-arm.

FIG. 4 shows a view in perspective of an example of an imaging system according to an embodiment of the invention including an automated guided vehicle supporting a C-arm and a manually guided vehicle supporting a protection cover, both vehicles being separated from each other. The medical operator 7 is holding a protection cover with the help of handles 23 and pushing this protection cover 2 toward the patient 6 and the gantry 1. The protection cover 2 is manually guided thanks to a vehicle 4 supporting this protection cover 2 and including free wheels 24, not shown on any figure. The protection cover 2 also includes a locking system 25 which is adapted to cooperate with the locking system 18 of the gantry in order to lock the protection cover 2 on the outer C 14 of the C-arm.

The protection cover 2 comprises a half ring 20 which is expandable into a full ring thanks to two retractable quarter rings, the upper quarter ring 21 and the lower quarter ring 22. Here, the retractable quarter rings 21 and 22 can be retracted inside the half ring 20. Practically, the half ring 20 shall be somewhat larger than half a circle, and the retractable quarter rings 21 and 22 shall be somewhat larger than the quarter of a circle. Whether on half ring 20 or on any of retractable quarter rings 21 or 22, the protection cover 2 includes an external circular wall 26, an internal circular wall 27, and two sides 28 and 29. When the protection cover 2 is installed, side 29 is closest to patient's feet than side 28.

Figure 5:
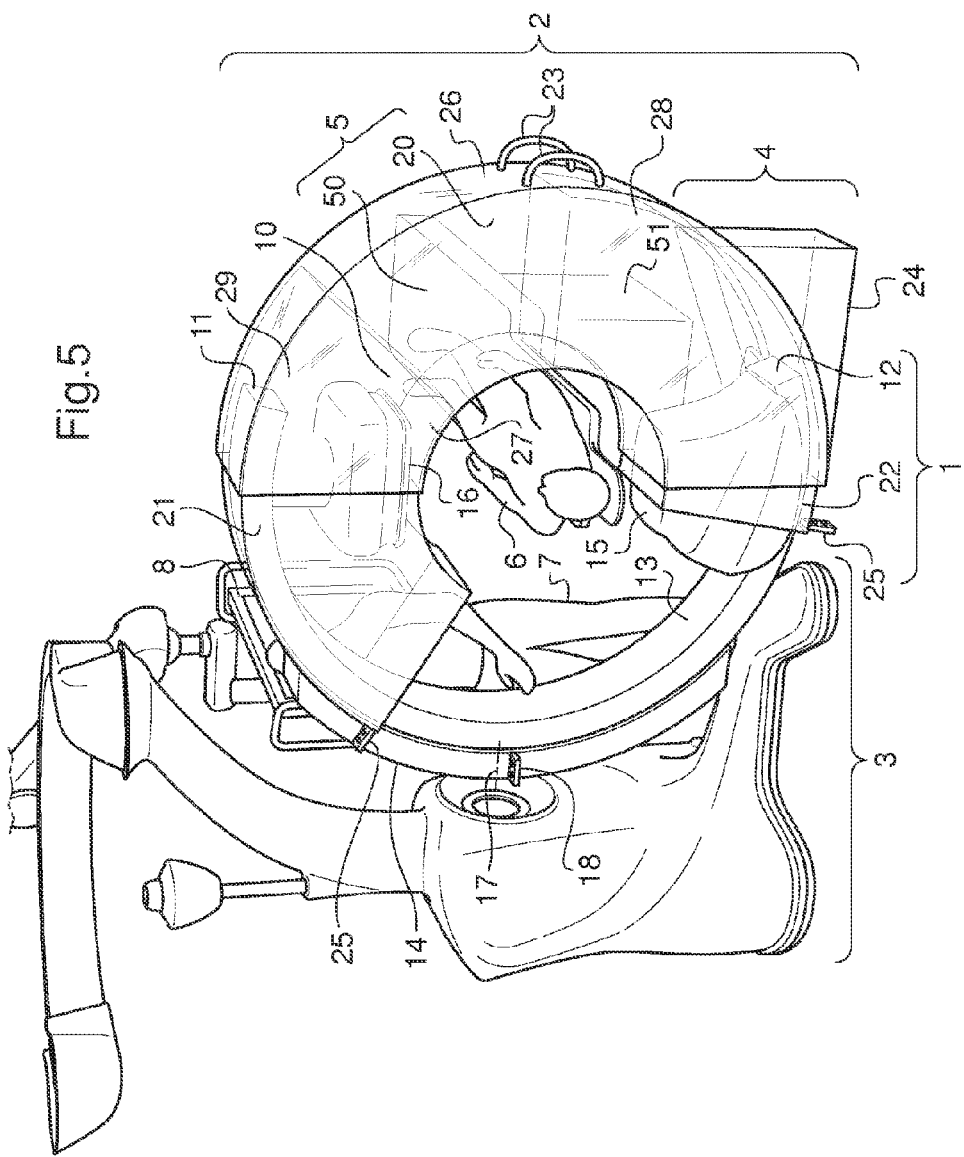
FIG. 5 shows a view in perspective of an example of an imaging system according to an embodiment of the invention including an automated guided vehicle supporting a C-arm and a manually guided vehicle supporting a protection cover, during installation of protection cover over C-arm.

FIG. 5 shows a view in perspective of an example of an imaging system according to an embodiment of the invention including an automated guided vehicle supporting a C-arm and a manually guided vehicle supporting a protection cover, during installation of protection cover over C-arm. When the protection cover 2 and the gantry 1 are face to face, both retracted quarter rings 21 and 22 are expanded so as to encompass completely the gantry 1. Upper quarter ring 21 rotates counter-clockwise whereas lower quarter ring 22 rotates clockwise.

Figure 6:
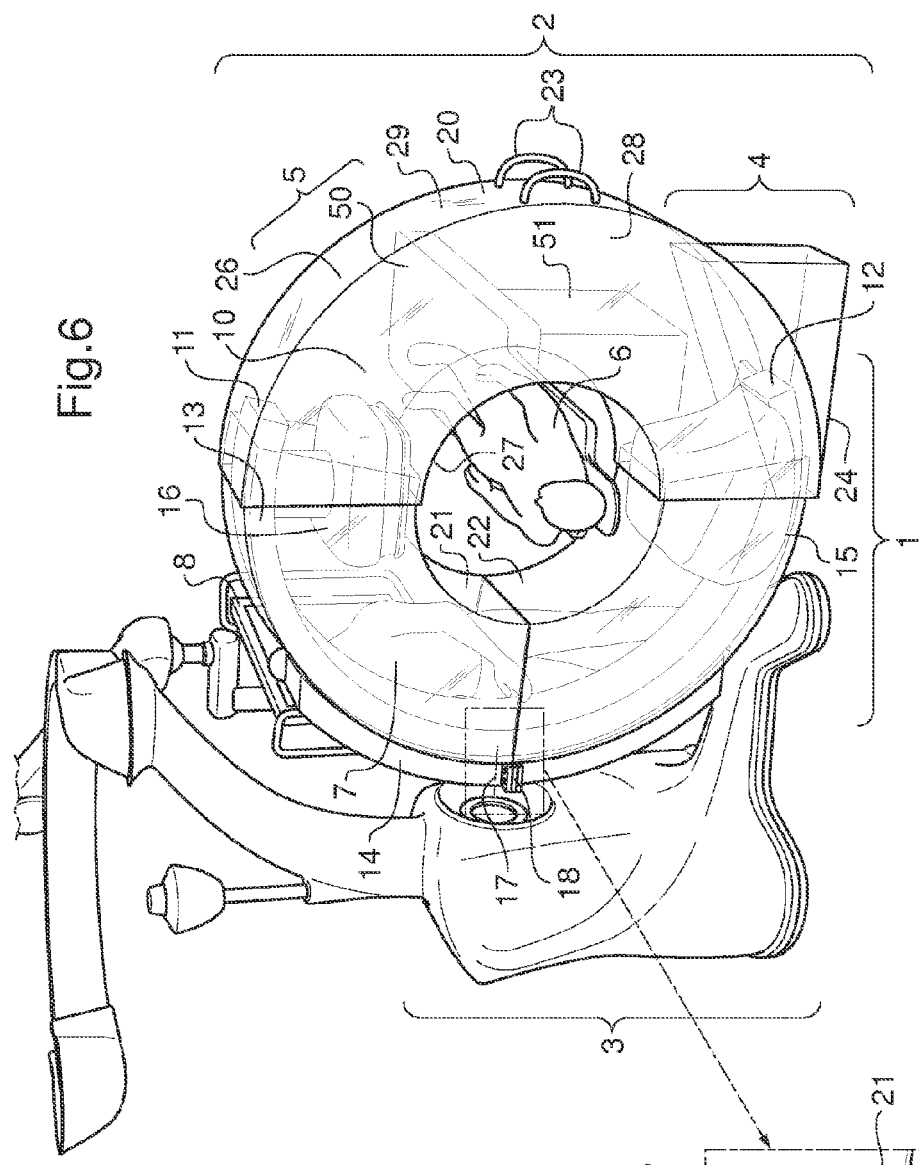
FIG. 6 shows a view in perspective of an example of an imaging system according to an embodiment of the invention including an automated guided vehicle supporting a C-arm and a manually guided vehicle supporting a protection cover, both vehicles being locked to each other.
Figure 7:
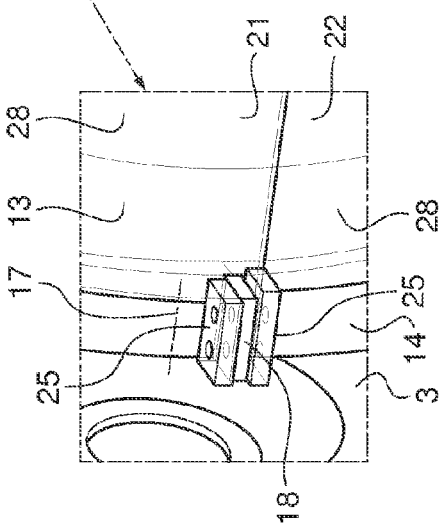
FIG. 7 shows a part of FIG. 6 detailing the locking system.

FIG. 6 shows a view in perspective of an example of an imaging system according to an embodiment of the invention including an automated guided vehicle supporting a C-arm and a manually guided vehicle supporting a protection cover, both vehicles being locked to each other. FIG. 7 shows a part of FIG. 6 detailing the locking system. Locking system 25 of protection cover 2 cooperates with locking system 18 of gantry 1 to lock the expanded quarter rings 21 and 22 of the protection cover 2 on the outer C 14 of C-arm. That way, protection cover 2 is made integral with gantry 1. The complete gantry 1 is now located inside the protection cover 2 so as to be fully protected against any collision risk from any external object, wherever it comes from.

FIG. 8 shows a view in perspective of an example of an imaging system according to an embodiment of the invention including an automated guided vehicle supporting a C-arm and a manually guided vehicle supporting a protection cover, during rotation of the C-arm covered by its protection cover. The double arrow shows the alternate rotation performed continuously by the inner C 13 of C-arm inside the protection cover 2. Inner C 13 of C-arm rotates first clockwise to reach extreme position already described with respect to FIG. 2. Inner C 13 of C-arm rotates then counter-clockwise to reach extreme position already described with respect to FIG. 3. Even if this alternate rotation is performed continuously at high rotation speed, there is no more collision risk, because of the expanded protection cover 2 encompassing completely the gantry 1, and encompassing notably all the rotating parts which are inner C 13, radiation source 15 and radiation detector 16. Encompassing completely radiation source 15 and radiation detector 16 is especially interesting since these are inward protruding parts which present high collision risk, in particular with the patient 6, for example with a moving arm of the patient 6.

FIG. 9 shows a view in perspective of an example of an imaging system according to an embodiment of the invention including an automated guided vehicle supporting a C-arm and a manually guided vehicle supporting a protection cover, showing the possible moves of both vehicles connected together so as to be able to move as one single vehicle. The three represented double arrows show the possible translation and rotation moves that the protection cover 2 made integral with the gantry 1 can perform in the horizontal plan of the ground. The protection cover 2 and the gantry 1 as well as their respective supporting vehicles 4 and 3 can be moved as if they were a single vehicle.

The gantry 1 and the tunnel 2 can also be tilted, by at least 10 degrees or even more, around a horizontal axis going through the middle of the tunnel 2. Advantageously, the gantry 1 will be actively tilted whereas the tunnel 2 will merely follow the tilt of the gantry 1.

FIG. 10 shows a view in perspective of an example of an imaging system according to an embodiment of the invention including an automated guided vehicle supporting a C-arm and a manually guided vehicle supporting a protection cover, showing the collision detection system of the protection cover. Circular sensitivity stripes 9 can act as a collision detection system of the protection cover 2. Those circular sensitivity stripes 9 will be implemented on the internal circular wall 27 of the protection cover 2, and, in an embodiment, at the junction between the circular internal wall 27 and the side 28 of the protection cover 2. In case any part of the table 5 or any part of the body of the patient 6 comes too close to the protection cover 2, alarm can be given. But anyway, collision would be much less harmful than a collision with any part of the rotating inner C 13 of C-arm as for example with the radiation source 15 or with the radiation detector 16. In an example, each part of the protection cover, 20, 21 and 22, has its own circular sensitivity stripe 9.

Figure 11:
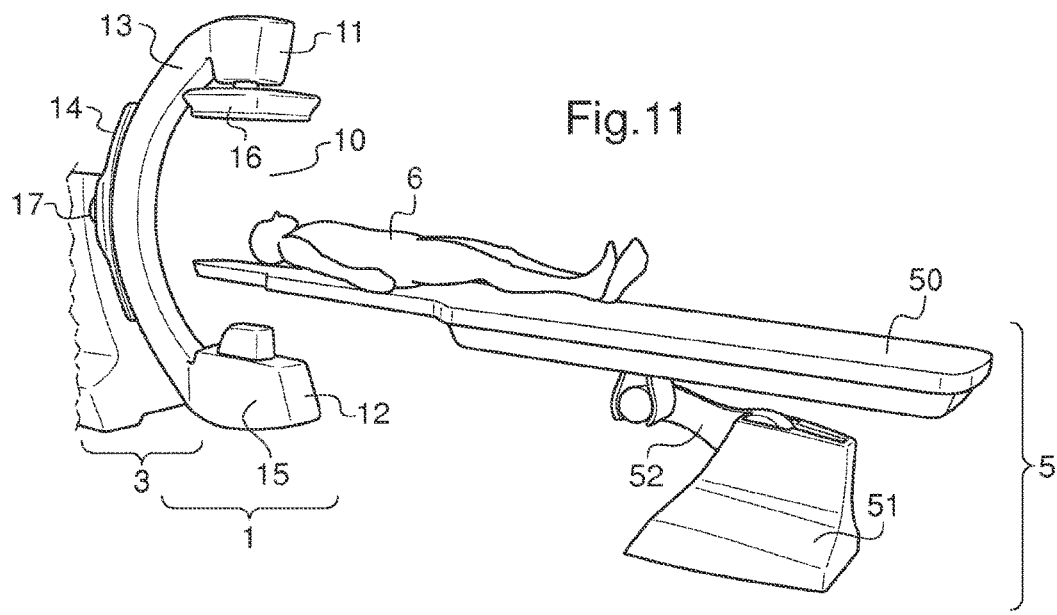
FIG. 11 shows a view in perspective of another example of an automated guided vehicle supporting a C-arm in a medical system according to another embodiment of the invention.

FIG. 11 shows a view in perspective of another example of an automated guided vehicle supporting a C-arm in a medical system according to another embodiment of the invention. The C-arm is oriented for axial three dimensional imaging. The top 50 of the table 5 is supported by the base 51 via an articulation 52. The vehicle 3 is an automated guided vehicle.

Figure 12:
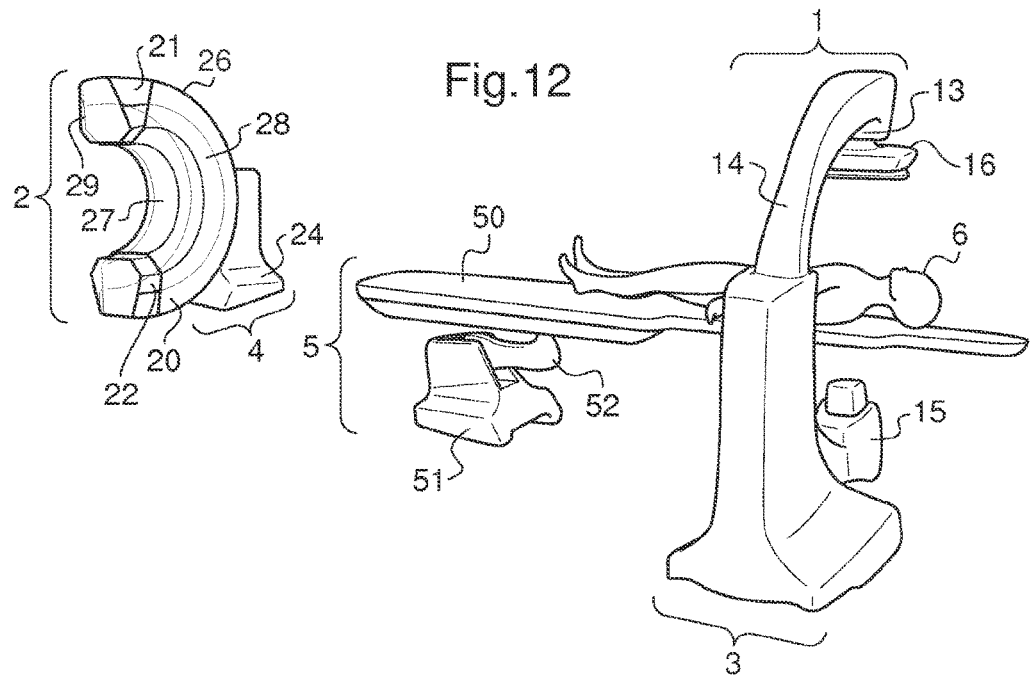
FIG. 12 shows a view in perspective of another example of an imaging system according to another embodiment of the invention including an automated guided vehicle supporting a C-arm and an automated guided vehicle supporting a protection cover, both vehicles being separated from each other.

FIG. 12 shows a view in perspective of another example of an imaging system according to another embodiment of the invention including an automated guided vehicle supporting a C-arm and an automated guided vehicle supporting a protection cover, both vehicles being separated from each other.

Figure 13:
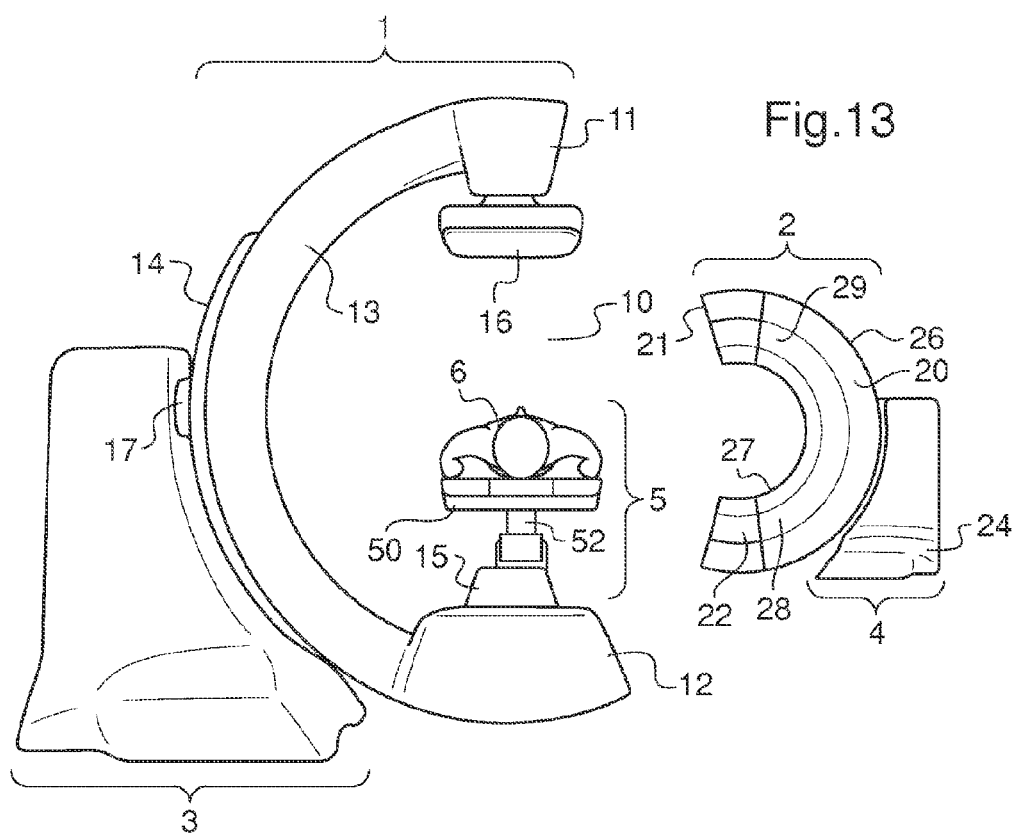
FIG. 13 shows a face view of another example of an imaging system according to another embodiment of the invention including an automated guided vehicle supporting a C-arm and an automated guided vehicle supporting a protection cover, both vehicles being separated from each other.

FIG. 13 shows a face view of another example of an imaging system according to another embodiment of the invention including an automated guided vehicle supporting a C-arm and an automated guided vehicle supporting a protection cover, both vehicles being separated from each other. Far away from automated guide vehicle 3 supporting C-arm, another automated guided vehicle 4 supporting the protection cover 2 is parked in the room at a parking position. The protection cover 2 is therefore no 10 hindrance if it is not needed. The protection cover 2 is parked in its retracted configuration, which means the upper 21 and lower 22 quarter rings are retracted inside the half ring 20 of the protection cover 2.

Figure 14:
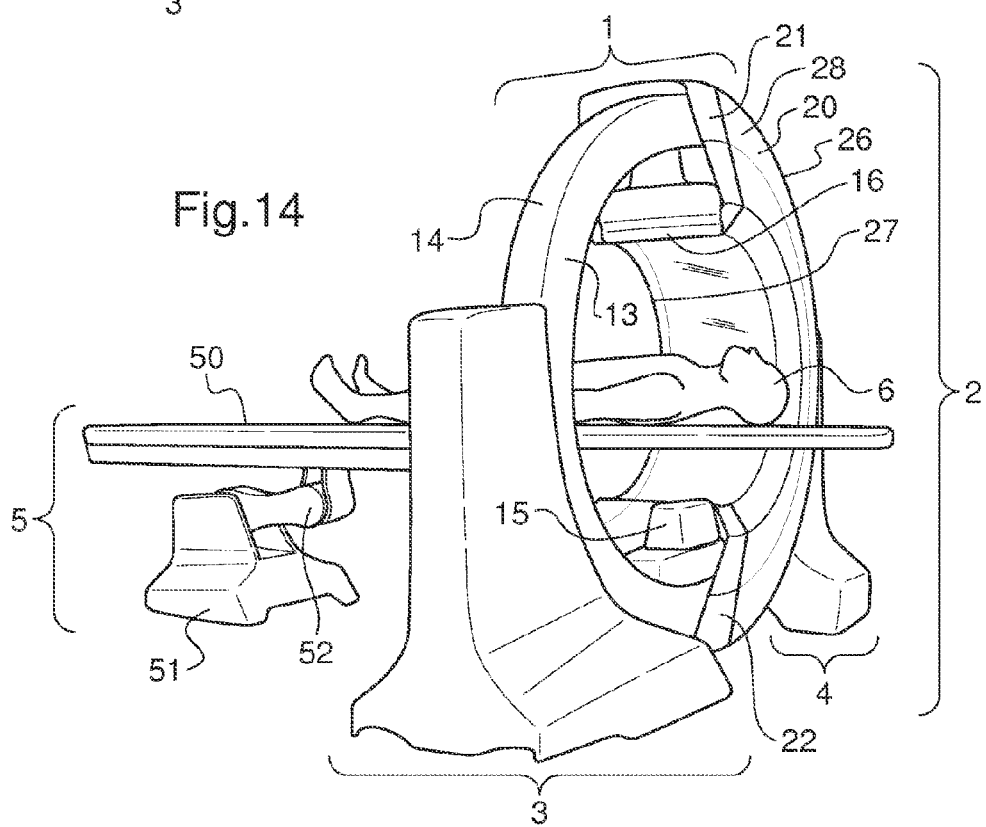
FIG. 14 shows a view in perspective of another example of an imaging system according to another embodiment of the invention including an automated guided vehicle supporting a C-arm and an automated guided vehicle supporting a protection cover, during installation of protection cover over C-arm.

FIG. 14 shows a view in perspective of another example of an imaging system according to another embodiment of the invention including an automated guided vehicle supporting a C-arm and an automated guided vehicle supporting a protection cover, during installation of protection cover over C-arm. Automated guided vehicle 4 has moved to come face to face with automated guided vehicle 3 so that protection cover 2 comes face to face with gantry 1. Both upper 21 and lower 22 retracted quarter rings will 20 be expanded from half ring 20 so as to encompass completely the gantry 1, and especially so as to encompass completely its rotating parts which are the inner C 13 as well as the radiation source 15 and detector 16. Quarter rings 21 and 22 will be locked on the outer C 14 of C-arm so that protection cover 2 is made integral with gantry 1. Each automated guided vehicle, either 3 or 25 4, have come from the sides of the table 5. These automated guided vehicles can even come when the exam is already started and when an anesthesia machine is already installed at the head of the patient.

Figure 15:
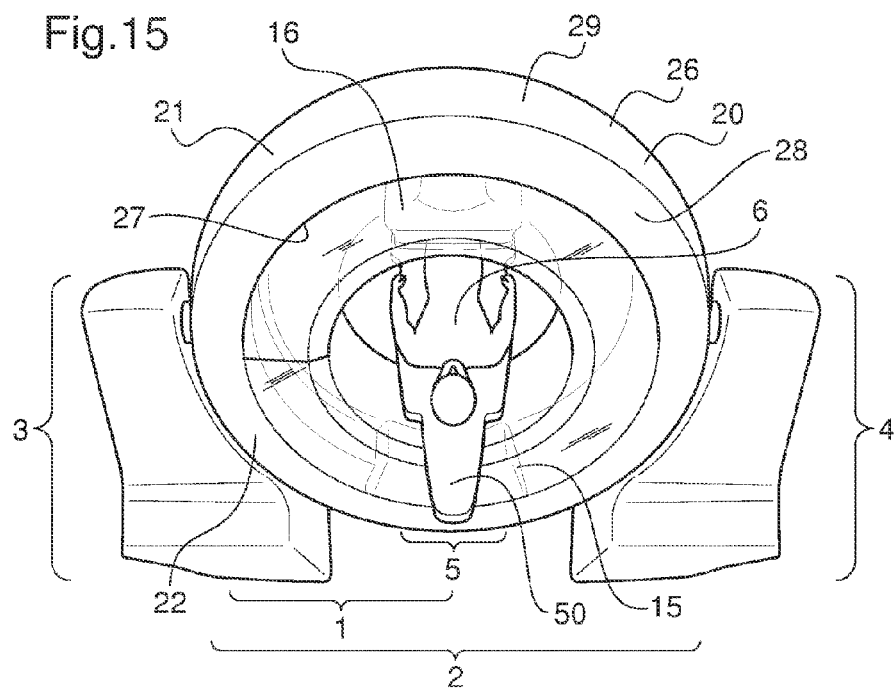
FIG. 15 and FIG. 16 show views in perspective of another example of an imaging system according to another embodiment of the invention including an automated guided vehicle supporting a C-arm and an automated guided vehicle supporting a protection cover, both vehicles being locked to each other, during rotation of the C-arm covered by its protection cover.
Figure 16:
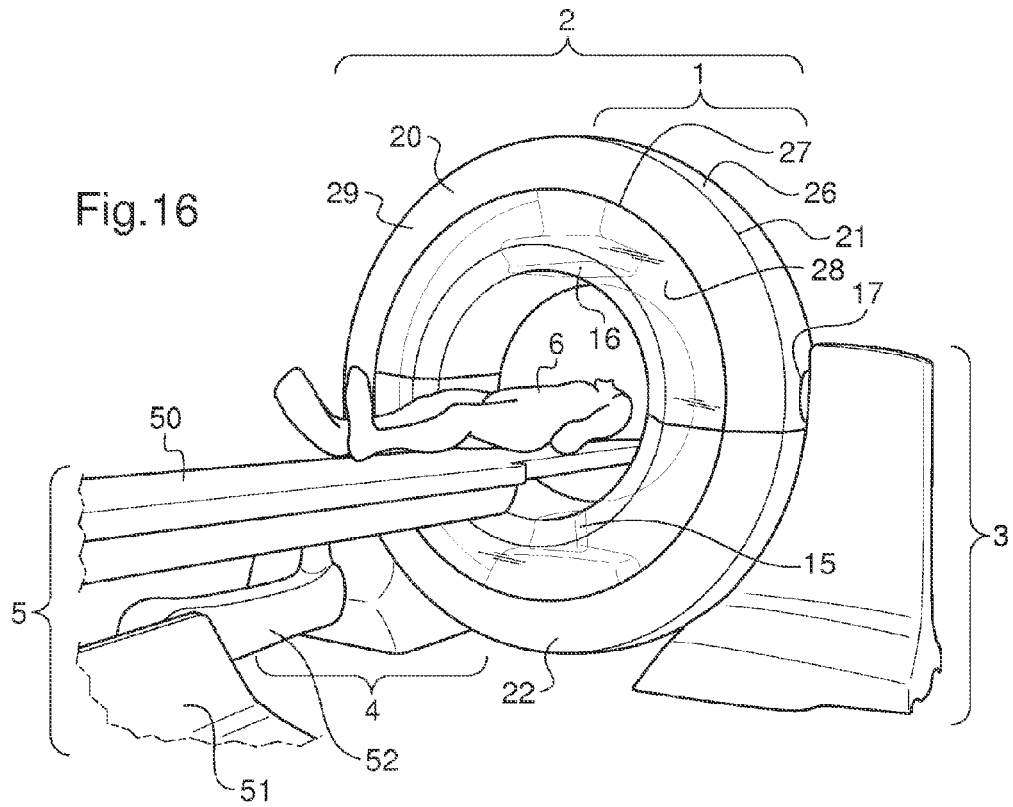

FIG. 15 and FIG. 16 show views in perspective of another example of an imaging system according to another embodiment of the invention including an automated guided vehicle supporting a C-arm and an automated guided vehicle supporting a protection cover, both vehicles being locked to each other, during rotation of the C-arm covered by its protection cover. Automated guided vehicle 4 and automated guided vehicle 3 can now move as a single vehicle. Both upper 21 and lower 22 retracted quarter rings have been expanded from half ring 20. The protection cover 2 now completely encompasses the gantry 1, and especially its rotating parts. Quarter rings 21 and 22 are locked on the outer C 14 of C-arm. Protection cover 2 is now integral with gantry 1. Inner C 13 of C-arm can rotate full speed within protection cover 2 with no more collision risk with any object external to protection cover 2. Especially the collision risk of any part of the body of the patient 6 with a protruding rotating part of C-arm, as the radiation source 15 or as the radiation detector 16, has been cancelled. Therefore no test phase rotating C-arm first at low speed is needed.

The invention has been described with reference to embodiments. However, many variations are possible within the scope of the invention.

The invention claimed is:
1. A medical imaging system, comprising:
   a C-arm supporting a radiation source and a radiation detector; and
   an external protection cover of said C-arm,
   wherein said C-arm and said cover are separable from each other and are respectively supported by two different vehicles when separated from each other,
   wherein said cover comprises an external wall and an internal wall configured to enclose said C-arm, said radiation source, and said radiation detector.
2. The medical imaging system according to claim 1, wherein said vehicles are both vehicles moving on the ground.
3. The medical imaging system according to claim 1, wherein said vehicle supporting said cover comprises a C-arm rotation guiding system.
4. The medical imaging system according to claim 1, wherein said vehicle supporting said C-arm is an automated guided vehicle.
5. The medical imaging system according to claim 1, wherein said vehicle supporting said C-arm comprises the full image chain from said radiation source to said radiation detector.
6. Medical imaging system according to claim 1, wherein said vehicle supporting said cover is an automated guided vehicle.
7. The medical imaging system according to claim 6, wherein said vehicle supporting said cover is configured to be automatically guided toward said vehicle supporting said C-arm.
8. The medical imaging system according to claim 7, wherein said vehicle supporting said cover is configured to be automatically guided toward said vehicle supporting said C-arm via a predetermined path.
9. The medical imaging system according to claim 7, wherein said vehicle supporting said cover is configured to be automatically guided toward said vehicle supporting said C-arm via a pre-calculated path which is automatically calculated from parking positions of both said vehicles.
10. The medical imaging system according to claim 1, wherein said vehicle supporting said cover is a manually guided vehicle.
11. The medical imaging system according to claim 10, wherein said vehicle supporting said cover is a manually moveable vehicle.
12. The medical imaging system according to claim 11, wherein said vehicle supporting said cover is a powerless vehicle.
13. The medical imaging system according to claim 10, wherein said cover comprises one or more free wheels.
14. The medical imaging system according to claim 1, wherein said cover comprises one or more handles.
15. The medical imaging system according to claim 1, wherein said vehicles are configured to be connected together so that an outer C of said C-arm and said cover can come to a rest relatively to each other.
16. The medical imaging system according to claim 1, wherein said vehicles are configured to be connected together so as to be able to move as one single vehicle.
17. The medical imaging system according to claim 1, wherein one of said vehicles is configured to be locked on the other of said vehicles via a locking system which locks one or more mobile parts of said cover on an outer C of said C-arm.

18. The medical imaging system according to claim 1, wherein said C-arm comprises a mobile inner C supporting said radiation source and said radiation detector, wherein said cover is removable from said C-arm, and wherein said cover is expandable into a tunnel encompassing the full rotation path of said inner C of said radiation source and of said radiation detector so as to protect said full rotation path both from inwards and from outwards of said inner C.

19. The medical imaging system according to claim 1, wherein said mobile inner C is rotary mobile so as to rotate alternatively clockwise and counterclockwise and or wherein said mobile inner C is rotary mobile so as to rotate continuously clockwise or to rotate continuously counterclockwise.

20. The medical imaging system according to claim 1, wherein both the C-arm and the protection cover are configured to be simultaneously tilted around a horizontal axis being a diameter of the C-arm.

\* \* \* \* \*